United States Patent [19]

Nashef

[11] Patent Number: 4,838,888

[45] Date of Patent: Jun. 13, 1989

[54] CALCIFICATION MITIGATION OF IMPLANTABLE BIOPROSTHESES

[75] Inventor: Aws S. Nashef, Huntington Beach, Calif.

[73] Assignee: Baxter Travenol Laboratories, Inc., Deerfield, Ill.

[21] Appl. No.: 39,295

[22] Filed: Apr. 17, 1987

[51] Int. Cl.$^4$ .............................................. A61F 2/24
[52] U.S. Cl. ......................................... 623/2; 8/94.11;
128/DIG. 8; 424/78; 514/165; 623/1; 623/66; 623/11
[58] Field of Search .................. 8/94.11; 106/218;
128/DIG. 8; 424/78; 514/165; 623/1, 2, 3, 11, 66

[56] References Cited

U.S. PATENT DOCUMENTS

| | | | |
|---|---|---|---|
| 3,625,745 | 12/1971 | Wright | 117/93.31 |
| 3,975,350 | 8/1976 | Hudgin et al. | 623/2 |
| 4,304,591 | 12/1981 | Mueller et al. | 71/93 |
| 4,323,358 | 4/1982 | Lentz et al. | 8/94.11 |
| 4,378,224 | 3/1983 | Nimni | 8/94.11 |
| 4,396,716 | 8/1983 | Marconi | 435/181 |
| 4,481,009 | 11/1984 | Nashef et al. | 8/94.11 |
| 4,553,974 | 11/1985 | Dewanjee | 8/94.11 |
| 4,648,881 | 3/1987 | Carpentier et al. | 623/11 |

FOREIGN PATENT DOCUMENTS 8401879  5/1984  PCT Int'l Appl. .................... 623/2

OTHER PUBLICATIONS

Oblath et al., "Prevention of Platelet Aggregation and Adherence to Prosthetic Vascular Grafts by Aspirin and Dipyridamole"; Surgery, Jul. 1978, pp. 37–44.

Lloyd et al.; "Coupling of Acrylic Polymers and Collagen by Use of Water Soluble Carbodiimide I" J. of Polymer Science:Polymer Chemistry Ed.; vol. 17, (1979) pp. 3459–3472.

Lloyd et al.; "Coupling of Acrylic Polymers and Collagen by Use of Water Soluble Carbodiimide II"; J. of Polymer Science:Polymer Chemistry Ed.; vol. 17; (1979) pp. 3473–3483.

*Primary Examiner*—Richard J. Apley
*Assistant Examiner*—Paul Prehilic
*Attorney, Agent, or Firm*—E. Anthony Figg; P. Flattery; M. Schiffer

[57] ABSTRACT

A process for treating biological tissue prior to implantation to mitigate the calcification of the tissue following implantation comprises incorporating acetylsalicylic acid into the tissue in an amount effective to reduce calcification of the tissue after it is implanted. In accordance with one embodiment, the process involves convalently binding the acetylsalicylic acid to the tissue via a coupling agent.

18 Claims, No Drawings

CALCIFICATION MITIGATION OF IMPLANTABLE BIOPROSTHESES

FIELD OF THE INVENTION

This invention is directed to a method of treating implantable bioprostheses to mitigate the calcification of the bioprostheses that typically occurs following implantation. More particularly, this invention is directed to a procedure wherein an implantable bioprosthesis is contacted with acetylsalicylic acid in an amount sufficient to reduce calcification of the bioprosthesis after it is implanted in the body of a living being.

BACKGROUND OF THE INVENTION

With the introduction of glutaraldehyde preservation of biological tissue, and in particular porcine bioprosthetic heart valves, it has become possible to: (a) overcome the poor performance of early formaldehyde-preserved implanted tissue valves; (b) discontinue the use of homograft valves; and (c) avoid the undesirable use of anticoagulants required to prevent thromboembolism associated with the use of non-bioprosthetic (mechanical) heart valves, especially in children. Not unlike similarly important discoveries, however, it appears that the glutaraldehyde-preserved bioprosthesis has created its own dilemma.

Although the relatively biologically inert glutaraldehyde-preserved valves of Carpentier and others have demonstrated excellent long-term durability in most instances, serious drawbacks such as tissue-fatigue and a propensity toward calcification have occured. Moreover, it was initially contemplated that children and adolescents would be among those deriving the greatest benefit from the glutaraldehyde-preserved bioprosthetic heart valves since the anticoagulants required with mechanical prosthesis could be eliminated. Results from an increasing number of recent clinical studies indicate that severe calcification of these tissues with relatively short-term failure is prevalent among children and adolescents. Thus, despite their long-term durability and overall reduced incidence of complications, these glutaraldehyde-preserved valves have been deemed by some to be unsuitable for use in children.

The causes of the calcification of these bioprostheses are not fully understood. It previously has been shown that a variety of factors, including calcium metabolism diseases, age and diet of the patient, and degeneration of tissue components such as collagen all are involved to a certain extent. Recently, the occurence of a specific calcium-binding amino acid (gamma carboxyglutamic acid), laid down after implantation of glutaraldehyde-preserved porcine xenographs, has been demonstrated, and it has been postulated to play a role in calcification. While calcification has been accompanied by degradative changes in the glutaraldehyde-treated collagen fibers of the implanted tissue, it remains unclear whether the dystrophic calcification is a cause or the result of tissue degeneration. Nevertheless, there has been a continued effort to determine the source of the calcification problem with implanted tissue.

Accordingly, it is an object of the present invention to provide a method for effectively reducing the calcification of implanted biological tissue.

SUMMARY OF THE INVENTION

In accordance with the present invention, there is disclosed a process for treating biological tissue prior to implantation which results in a mitigation of calcification of the tissue following implantation. The process comprises incorporating acetylsalicylic acid into biological tissue in an amount effective in reducing calcification of the tissue after implantation. In accordance with one embodiment, the process comprises covalently binding the acetylsalicylic acid to the tissue via a coupling agent.

DETAILED DESCRIPTION OF THE INVENTION

In accordance with the present invention, it is contemplated that various types of implantable biological tissue derived from numerous animal sources and parts of the anatomy can be made resistant to calcification. Thus, the tissue can be derived from various sources such as, but not limited to, bovine, porcine, horse, sheep, kangaroo, or rabbit; and can include tendons, ligaments, heart valves, or tissue used to construct heart valves such as dura mater and pericardium. It is further contemplated that tissue used for augmentation such as skin patches, pericardial patches, aortic patches, and tympanic membranes is suitable in the present invention.

In accordance with the present invention, the tissue may be stored and processed in accordance with conventional well-know conditions and may be fixed (tanned) conventionally in from about 0.2 to about 0.6 weight percent and preferably from about 0.5 to about 0.7 weight percent glutaraldehyde in either phosphate-buffered solutions, or phosphate-free buffers as described hereinafter. The tissue handling conditions as conventionally known are not considered part of the present invention unless otherwise stated. Likewise, tissue may be sterilized as taught in the art. For example, the tissue may be sterilized in 0.625 percent glutaraldehyde or from about 4 to about 5 percent formaldehyde. Optionally, the formaldehyde solution also may contain ethanol and a surfactant such as sorbitan monooleate polyoxyethylene (tween-80).

Although not wishing to be bound to a particular theory, it is hypothesized that, in addition to the various factors set forth above, tissue calcification also may be the result of an inflammatory response or platelet aggregation on the surface of the implant which may lead to micro changes in pH or localized enzyme effects that lead to hydroxyappatite nucleus formation and eventual calcification. It surprisingly has been found that when acetylsalicylic acid (aspirin), a compound known for its anti-inflammatory and anti-platelet action, is incorporated into implantable biological tissue, and the treated biological tissue subsequently is implanted into an animal, calcification of the treated tissue is mitigated. This sustained mitigation of calcification provides a method of increasing the durability of implanted tissue. In a preferred embodiment of the present invention, the implantable biological tissue comprises heart valve bioprostheses.

In accordance with the present invention, acetylsalicylic acid can be chemically bonded to implantable biological tissue or impregnated into the tissue by inclusion within the interstices of the tissue to form a physical or mechanical bond. Covalent binding has the advantage that the acetylsalicylic acid will not be displaced from the tissue after implantation and is thus the preferred technique.

The covalent bonding of the acetylsalicyclic acid to the biological tissue desirably is achieved through the use of coupling agents, although the acetylsalicylic acid can be coupled directly to the tissue, especially if fresh tissue is used. In accordance with a preferred embodiment of the present invention, diamines are used as the coupling agents with the aid of an activating factor, such as a carbodiimide. The diamine binds to carboxyl groups of the biological tissue. Although diamines are preferred coupling agents, also known as spacers, other compounds with free terminal amino or carboxyl groups also can be used. Examples of this type of coupling are illustrated by Lloyd and Burns in *Journal of Polymer Science: Polymer Chemistry Edition,* Vol. 17, pp. 3459-3483 (1979). Preferred diamines in accordance with the present invention include those having the formula $R-(NH_2)_2$ wherein R is an aliphatic group having straight, branched, or cyclic chain, or an aromatic group. It is contemplated that the chain length or bulkiness of R should be such that the diamine can freely diffuse within the protein network of the tissue. Preferably the diamine should be water-soluble. The most preferred diamine in accordance with the present invention is ethylenediamine.

Generally, the biological tissue is contacted with a solution of diamine, or other coupling agent which has a concentration of from about 0.01M to about 0.5M. Preferably the concentration is about 0.05M to about 0.1M. The coupling reaction usually is allowed to proceed for about 20 minutes to about 60 minutes. The pH of the solution is maintained at about 4 to about 5, and preferably at about 4.75.

As mentioned above, a water soluble carbodiimide may be added to the solution of diamine in contact with the biological tissue to cross-link the tissue and diamine. The carbodiimides have the general formula $R-N=C=N-R'$, wherein R and R' are hydrocarbyl groups. The length of R and R' should be such that the carbodiimide is water soluble. Preferred carbodiimides include 1-ethyl-3-(3-dimethylaminopropyl)-carbodiimide and dicyclohexyl carbodiimide. It is believed that the carbodiimide forms amide bonds by activating carboxyl groups to allow reaction with amino groups. The crosslinking generally occurs at a carbodiimide concentration of about 0.1 to about 1 molar, preferably about 0.4 to about 0.8 molar. The pH desirably is maintained at about 4 to about 5, and preferably is maintained at about 4.75. The cross-linking reaction generally is allowed to proceed for about 20 minutes to about 60 minutes. After the reaction is completed, the tissue can be washed to remove excess reagents. Desirably, the rinsing solution is a balanced electrolyte solution that has a neutral pH.

Following this, the acetylsalicylic acid can be coupled to the, tissue via the coupling agent. Carboxyl groups of the acetylsalicylic acid can couple to amino groups on the tissue that were introduced by the coupling of the diamine. The acetylsalicylic acid can be dissolved first in a small amount of an alcohol, such as ethyl or iso-propyl, and then diluted to the desired final volume with water. Generally, effective concentrations of acetylsalicylic acid have been found to range from about 0.005M to about 0.2M; a preferred concentration is about 0.1M. The treated tissue is contacted with the solution of acetylsalicylic acid. The pH of the solution desirably is adjusted with HCl or sodium hydroxide to be in the range of about 4 to about 5; a preferred pH is about 4.75. The reaction is allowed to proceed for about 20 minutes to about 60 minutes.

As in the first step of this process, a carboxylactivating agent, such as the water soluble carbodiimides suggested above, may be added to the acetylsalicylic acid solution. Effective concentrations of cross-linking agents are as set forth above, and the cross-linking reactions may be allowed to proceed for about 20 minutes to about 60 minutes.

Following this second step of the process of the present invention, excess reagents again desirably are rinsed from the treated biological tissue.

In accordance with the present invention, it is preferable to store, fix, and sterilize the tissue within a tissue-stabilizing pH range; that is, within a pH range that is not deleterious to the tissue components. A preferred pH range is from about 7.0 to about 7.6, and a more preferred pH range is from about 7.1 to about 7.4. The most preferred pH in accordance with the present invention is 7.3.

Buffers used in accordance with one embodiment of the present invention are preferably stable, noninteracting with the stabilization process, and have a buffering capacity sufficient to maintain an acceptable pH, particularly during the fixation of the tissue. The choice of the appropriate buffer, and its concentration will depend upon specific tissue preparation conditions; variations of which have been introduced by several manufacturers. The buffers can be either conventional 0.01–0.02M phosphate-buffered saline (PBS) or phosphate-deficient solutions such as those containing less phosphate than these 0.01 to 0.02M PBS solutions, and preferably less than about 0.001 to about 0.002M phosphate. Preferred buffers in accordance with the present invention include borate, carbonate, bicarbonate, cacodylate (found to be nontoxic in animals), and other synthetic, artificial, or organic buffers such as HEPES, N-2-hydroxyethylpiperazine-N'2-ethanesulphonic acid; MOPS, 2-(N-morpholino) propane-sulfonic acid; and PIPES, 1,4-piperazinediethanesulphonic acid.

Preferably, the buffered or unbuffered solutions used in accordance with the present invention should not interfere with the tissue stabilizing process afforded by fixing agents such as glutaraldehyde. That is, they should not react with the fixing agent or prevent the fixing agent from achieving proper fixation of the tissue. Illustrative of this are buffers containing primary and secondary amines, such as tris(hydroxymethyl)aminomethane (Tris), which are known to react with the aldehyde groups of glutaraldehyde or formaldehyde and thus interfere with the normal tissue stabilization process.

In accordance with the present invention, the tissue can be fixed (tanned) in 0.625 weight percent glutaraldehyde.

The present invention is further illustrated by the following examples which are not intended to be limiting:

EXAMPLE 1

This example describes the preparation of implantable biological tissue according to the present invention. Porcine aortic valve leaflet tissue (5 grams, wet weight), which had been previously tanned in 0.625% glutaraldehyde, was rinsed three times in normal saline (2 minutes per rinse). The rinsed tissue was submerged in 28 mls. of 0.1M ethylene diamine, pH 4.75 for thirty minutes. The pH was monitored and adjusted as necessary.

After soaking the tissue in the ethylene diamine solution, 3 grams of a water-soluble carbodiimide (1-ethyl-3-(3-dimethylaminopropyl)carbodiimide) were added to the solution containing the tissue. The pH of this mixture was maintained at 4.75, and the reaction between the tissue, the ethylenediamine and the carbodiimide was allowed to proceed for 30 minutes at room temperature.

Following the reaction, the tissue was removed from the solution and rinsed three times with 100 ml. of normal saline (2 minutes per rinse).

A 0.1M solution of aspirin was prepared by dissolving aspirin in a small volume of ethanol, then diluting the volume with water. The tissue from the above reaction was placed in the 28 ml. of the aspirin solution. After 30 minutes of equilibration, 2 grams of the same carbodiimide used above were added to the solution, and the pH was maintained at 4.75 for thirty minutes at room temperature. The tissue was withdrawn and rinsed with normal saline as described above. The tissue was then stored in 0.625% glutaraldehyde solution, pH 7.4 for at least two weeks. Prior to use, the tissue was sterilized in 4% formaldehyde or a solution of 4% formaldehyde, 22.5% ethanol, 11.3 mM (1.5 weight percent) sorbitan monooleate polyoxyethylene and 0.26 grams/liter $MgCl_2 \cdot 6H_2O$ at pH 7.3 and 35° C.

EXAMPLE 2

Porcine aortic valve leaflet tissue prepared as described in example 1 were implanted in growing rabbits. Tissues that had not been treated with aspirin were also implanted in a second group of animals, which were used as controls. Samples of the tissues were removed from the animals at 2, 3, 4, 5 and 6 weeks and anlayzed for calcium. Treatment of the tissue with aspirin resulted in significant mitigation of calcification.

I claim:

1. A process for treating animal biological tissue prior to implantation in an animal to reduce calcification of said tissue following implantation, which comprises:
    (a) fixing said tissue under tissue-fixing conditions, and
    (b) contacting said tissue with a solution of acetylsalicylic acid for a time sufficient to covalently bind said acetylsalicylic acid directly to said tissue in an amount effective to reduce calcification of said tissue after implantation.

2. The process of claim 1, wherein said biological tissue is tendon, ligament, heart valve, dura mater or pericardium.

3. The process of claim 1, wherein said biological tissue is fixed with glutaraldehyde.

4. The process of claim 1, wherein the concentration of acetylsalicylic acid is from about 0.05M to about 0.2M.

5. The process of claim 4, wherein said tissue is contacted with said acetylsalicylic acid solution for about 20 minutes to about 60 minutes.

6. A process for treating animal biological tissue prior to implantation in an animal to reduce calcification of said tissue following implantation, which comprises:
    (a) fixing said tissue under tissue-fixing conditions,
    (b) contacting said fixed tissue with a solution of a coupling agent for a time sufficient to covalently bond said coupling agent to said tissue, and
    (c) contacting said tissue with a solution of acetylsalicylic acid for a time sufficient to covalently bond said acetylsalicylic acid to said tissue through said coupling agent in an amount effective to reduce calcification of said tissue after implantation.

7. The process of claim 6, wherein said coupling agent is a diamine.

8. The process of claim 6, wherein said tissue is contacted with a carbodiimide between steps (b) and (c) and after step (c).

9. The process of claim 7, wherein said diamine has the formula $R-(NH_2)_2$, wherein R is an aliphatic group having a straight, branched or cyclic chain or is an aromatic group.

10. The process of claim 9, wherein said diamine is ethylenediamine.

11. The process of claim 6, wherein said biological tissue is a tendon, ligament, heart valve, dura mater or pericardium.

12. The process of claim 6, wherein said biological tissue is fixed with glutaraldehyde.

13. The process of claim 6, wherein the concentration of coupling agent in solution is from about 0.01M to about 0.5M.

14. The process of claim 6, wherein the concentration of acetylsalicylic acid is from about 0.05M to about 0.2M.

15. The process of claim 14, wherein the tissue is contacted with said acetylsalicylic acid solution for a time of about 20 minutes to about 60 minutes.

16. The process of claim 6, wherein said tissue is maintained at a pH of from about 4 to about 5 as it is contacted with said coupling agent and with said acetylsalicylic acid.

17. A process for treating animal biological tissue prior to implantation in an animal to reduce calcification of said tissue following implantation, which comprises:
    (a) fixing said tissue under tissue fixing conditions, and
    (b) contacting said tissue with a solution of acetylsalicylic acid for a time sufficient to impregnate said acetylsalicylic acid in said tissue in an amount effective to reduce calcification of said tissue after implantation.

18. Biological tissue having a reduced tendency toward calcification after implantation in an animal, said tissue being covalently bonded to acetylsalicyclic acid in accordance with the process of claim 1 or claim 6.

* * * * *